(12) United States Patent     (10) Patent No.: US 11,464,665 B2
Kelly     (45) Date of Patent: Oct. 11, 2022

(54) CONTACT POINT REDUCTION GARMENT

(71) Applicant: Sanford Health, Sioux Falls, SD (US)

(72) Inventor: Patrick W. Kelly, Sioux Falls, SD (US)

(73) Assignee: Sanford Health, Sioux Falls, SD (US)

( * ) Notice: Subject to any disclaimer, the term of this patent is extended or adjusted under 35 U.S.C. 154(b) by 0 days.

(21) Appl. No.: 15/251,544

(22) Filed: Aug. 30, 2016

(65) Prior Publication Data

US 2017/0056233 A1     Mar. 2, 2017

Related U.S. Application Data

(60) Provisional application No. 62/212,250, filed on Aug. 31, 2015, provisional application No. 62/308,410, filed on Mar. 15, 2016.

(51) Int. Cl.
| | |
|---|---|
| *A61F 5/32* | (2006.01) |
| *A61F 5/34* | (2006.01) |
| *A61M 39/22* | (2006.01) |
| *A61F 5/01* | (2006.01) |
| *A61F 13/06* | (2006.01) |

(52) U.S. Cl.
CPC .............. *A61F 5/32* (2013.01); *A61F 5/0109* (2013.01); *A61F 5/0111* (2013.01); *A61F 5/0118* (2013.01); *A61F 5/34* (2013.01); *A61F 13/066* (2013.01); *A61M 39/22* (2013.01)

(58) Field of Classification Search
CPC .......... A61F 2013/15024; A61F 13/069; A61F 13/08; A61F 13/064; A61F 13/066; A61F 13/067; A61F 13/068; A61F 2013/00823; A61F 2013/00825; A61F 2013/0028;
(Continued)

(56) References Cited

U.S. PATENT DOCUMENTS 3,266,058 A * 8/1966 Guttman ............... A61F 13/069
                                                                        2/239
5,154,690 A * 10/1992 Shiono .................. A61F 5/0102
                                                                        602/21

(Continued)

FOREIGN PATENT DOCUMENTS

| CA | 2 888 104 | * | 4/2013 |
|---|---|---|---|
| CA | 2 888 104 A1 | * | 4/2013 |

(Continued)

OTHER PUBLICATIONS

Website for Silipos http://www.silipos.com/products/symes-gel-liner, retrieved Jan. 27, 2017.

(Continued)

*Primary Examiner* — Camtu T Nguyen (74) *Attorney, Agent, or Firm* — McDonnell Boehnen Hulbert & Berghoff LLP (57) ABSTRACT

The present disclosure provides a wearable garment comprising (a) a sheath having a first end and a second, wherein the sheath defines a cavity in a wearable position, wherein the sheath has a first opening at the first end, and wherein the sheath comprises a first material, and (b) one or more relief zones coupled to the sheath, wherein the relief zones comprise a second material, wherein a pressure distribution of the second material is greater than a pressure distribution of the first material.

17 Claims, 4 Drawing Sheets

(58) Field of Classification Search
CPC .... A61F 2013/0093; A61F 2013/00093; A61F 2013/00119
USPC .......................................... 602/13, 62, 65, 75
See application file for complete search history.

(56) References Cited

U.S. PATENT DOCUMENTS

| | | | |
|---|---|---|---|
| 5,185,000 | A | 2/1993 | Brandt |
| RE34,661 | E * | 7/1994 | Grim ........................ A43B 7/20 128/DIG. 20 |
| 7,060,086 | B2 * | 6/2006 | Wilson ...................... A61F 7/02 602/61 |
| 2004/0039432 | A1 * | 2/2004 | Warriner ................... A61F 7/02 607/108 |
| 2005/0107728 | A1 | 5/2005 | Vetters |
| 2006/0085894 | A1 * | 4/2006 | Yakopson ............... A61F 13/08 2/239 |
| 2008/0086070 | A1 * | 4/2008 | Meehan ................ A61F 5/0104 602/26 |
| 2008/0249454 | A1 * | 10/2008 | Mills ....................... A61F 13/08 602/63 |
| 2010/0056973 | A1 * | 3/2010 | Farrow .................. A61F 13/08 602/63 |
| 2010/0180358 | A1 * | 7/2010 | Drummond .............. A41D 7/00 2/244 |
| 2013/0152285 | A1 * | 6/2013 | Sutton ................ A41D 13/0155 2/455 |
| 2014/0088475 | A1 * | 3/2014 | Bue, Jr. .................. A61H 1/006 601/134 |
| 2014/0259260 | A1 * | 9/2014 | Behrend ................ A41D 13/05 2/22 |
| 2016/0038346 | A1 * | 2/2016 | Collins .................. A41B 11/08 602/63 |
| 2016/0242964 | A1 * | 8/2016 | Rapp ................... A61F 13/0273 |

FOREIGN PATENT DOCUMENTS

| | | |
|---|---|---|
| EP | 0496071 A1 | 7/1992 |
| WO | 2010/025186 A1 | 3/2010 |
| WO | 2012/142155 A2 | 10/2012 |
| WO | 2013/063554 A1 | 5/2013 |
| WO | 2014/152372 A1 | 9/2014 |

OTHER PUBLICATIONS

Website for Silipos http://www.silipos.com/products/skate-bite-protector, retrieved Jan. 27, 2017.
International Search Report for corresponding PCT application No. PCT/US2016/049436 dated Dec. 2, 2016.

* cited by examiner

CONTACT POINT REDUCTION GARMENT

RELATED APPLICATIONS

This application claims priority to (i) U.S. Provisional Application No. 62/212,250 entitled "Contact Point Reduction Garment," filed on Aug. 31, 2015, and (ii) U.S. Provisional Application No. 62/308,410 entitled "Contact Point Reduction Garment," filed on Mar. 15, 2016, both of which are hereby incorporated by reference in their entirety.

BACKGROUND THE INVENTION

Wounds may be defined as damage to the skin and underlying tissues. Such wounds often happen in patients with diabetes or circulatory impairment. The circulatory impairment can manifest as lymphedema, venous insufficiency, or elevated pressure which can compromise localized microvasculature, as examples. Lymphedema and venous insufficiency are a result of fluid not being returned to the heart properly. Localized elevated pressure, which results in pressure ulcers, can result from flow being stopped through the microvasculature, where nutrients are exchanged between the blood and tissue.

Venous ulcers often accompany varicose veins and most often affect the distal leg and ankle. They are usually painful, large in size, and exudative. Venous ulcers may become recurrent at times and can have varying depths. They occur from blood pooling in the ankle which creates a chronic tension on the delicate skin of the ankle. Such wounds typically occur on the sides of the ankle. Recommended ways for preventing venous ulcers include elevating the extremity and also applying graduated compressive stockings. Elevating the extremity requires applying a force to the underside of the heel. Unfortunately this can create areas of localized pressure on the heel. To prevent this, heel pillows have been developed. Compressive stockings can also create a risk of creating a pressure ulcer over any of the bony prominences of the foot should the localized pressure created exceed the capillary pressure and thus create localized regions of ischemia.

Pressure ulcers can occur anywhere following prolonged periods of sustained pressure. Such pressure ulcers can become life/ limb threatening. In elderly patients, the skin on the distal extremity can be extremely fragile and thin. Further, the foot and ankle has several bony prominences which may create areas of increased pressures when the foot is wrapped or when the patient lies in bed for a prolonged period of time. When a patient is confined to bed rest after a medical procedure, tissue necrosis may occur due to various externally applied forces to the lower extremities of the patient. For example, simple pressure from the patient's foot resting on a mattress can lead to tissue necrosis in the bony areas of the foot. In order to prevent pressure ulcers, heel pillows (noted above) and gel filled bandages have been developed. Heel pillows distribute forces thereby effectively reducing localized pressure but are associated with certain disadvantages. For example, heel pillows are not intended for use during the act of walking and only protect the heel region. Because of the difficulty of walking with a heel pillow, patient compliance with heel pillows is typically very poor. The gel in bandages offloads force from bony prominences and also helps to reduce shear stress and friction on the skin that often lead to wound formation. Hospitals also develop protocols for periodically turning patients to prevent prolonged localized regions of pressure and ultimately pressure ulcers that may result.

SUMMARY OF THE INVENTION

Wounds of the local extremities can often be multifactorial with both arterial and venous contributing factors. The inventor recognized that compression may be needed but is ill-advised if there is some arterial compromise or tissue fragility. Accordingly, the invention described herein provides an apparatus that may be used to distribute forces over these areas to effectively reduce regions of high pressure and prevent pressure ulcers. For example, the disclosed garment is configured to be worn on a distal extremity to encourage the distribution of forces and reduction of pressure over the bony prominences of the body.

More specifically, as mentioned above, if local applied pressure exceeds the capillary pressure of a patient due to confined bed rest or compressive bandages, for example, localized ischemia may result and tissue necrosis may follow. To address this, a contact point reduction garment is provided herein to address tissue necrosis in the extremities. In one example, the contact point reduction garment is a wearable garment that may include one or more relief zones positioned over the bony areas of the foot to help to move some of the pressure of the bandage away from the bony area and transfer it to the softer tissue areas of the foot. Thus, the invention may take the form of a compression sock or hose that has padding built into these relief zones, thereby reducing the occurrence of tissue necrosis in bedridden or ambulatory individuals. In another example, the wearable garment described herein may be used in the region of the knee and may prevent excess pressure around the hamstring tendon or gracilis muscle, for example. In yet another example, the wearable garment described herein may be used in the region of the elbow and may prevent excess pressure around the elbow.

Thus, in one aspect, the present disclosure provides a wearable garment comprising (a) a sheath having a first end and a second, wherein the sheath defines a cavity in a wearable position, wherein the sheath has a first opening at the first end, and wherein the sheath comprises a first material, and (b) one or more relief zones coupled to the sheath, wherein the relief zones comprise a second material, wherein a pressure distribution of the second material is greater than a pressure distribution of the first material.

These as well as other aspects, advantages, and alternatives, will become apparent to those of ordinary skill in the art by reading the following detailed description, with reference where appropriate to the accompanying drawings.

DETAILED DESCRIPTION OF THE INVENTION

Exemplary devices and methods are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

As used herein, with respect to measurements, "about" means +/−5%.

As used herein, "pressure distribution" means a maximum pressure value experienced in response to any non-physiological force applied to a lower extremity of a user.

As used herein, "bilateral" means of, at, toward, or from the side or sides of the human body.

As used herein, "medial" means situated in the middle or near the median plane of the body.

As used herein, "distal" means situated away from the center of the body or from the point of attachment.

As used herein, "posterior" means further back in position, of or near the rear or hind end of the body or a part of it.

As used herein, "proximal" means situated nearer to the center of the body or the point of attachment.

As used herein, "anterior" means nearer the front, especially situated in the front of the body or nearer the head.

As used herein, "cuneiform" means bones that are in the mid-foot and attached to the navicular bone on the proximal extent and the metatarsals on the distal extent. The cuneiforms are attachment points for several ligaments and are involved in articulation of the joints of the foot.

As used herein, "metatarsal bones" means bones that are connected to the proximal phalanges on the distal end and the cuneiform bones and cuboid bone on the proximal end. The metatarsal bones are divided into three parts: the base, body, and head. The head is closest to the toes.

As used herein, "scaphoid (navicular) tubercle" means a bony prominence that extends from the medial portion of the foot where the tibialis posterior muscle attaches. The navicular bone articulates proximally with the talas, distally with the three cuneiform bones, and laterally with the cuboid.

As used herein, "malleolus" means a bony projection on each side of the human ankle.

As used herein, "medial malleolus" means the prominence on the inner side of the ankle formed by the lower end of the tibia.

As used herein, "lateral malleolus" means the prominence on the outer side of the ankle, formed by the lower end of the fibula.

As used herein, "relief zone" means a portion of the garment that is intended to distribute compressive forces on the foot effectively reducing pressure.

As used herein, "first end" means the proximal end of the garment, away from the toes of the feet.

As used herein, "second end" means the distal end of the garment or the end in close proximity to the toes of the feet.

As used herein, "ischemia" means an inadequate blood supply to an organ or part of the body, in this case the tissue of the foot around a bony prominence.

As used herein, "capillary pressure" means a pressure in the blood near the capillary, which is reduced substantially, to approximately 2 kPa, from blood pressure allowing the transfer of nutrients and waste products.

As used herein, "inferior glue" means a glue that creates a nonpermanent reusable mechanical connection between two surfaces.

With reference to the Figures, FIGS. 1-6 illustrate a wearable garment 100 according to an example embodiment. In particular, as shown in FIGS. 1-6, the wearable garment 100 may include a sheath 102 having a first end 104 and a second end 106. The sheath includes a first material and defines a cavity 110 in a wearable position, and the sheath 102 has a first opening 112 at the first end 104. The first material may comprise a breathable matrix, a cotton material, Polytetrafluoroethylene (PTFE), polyester, an elastic material, or combinations thereof, among other possibilities. The first material may include an elastic property such that the sheath 102 is configured to expand to receive an appendage of a user, and thereafter retract to conform to the appendage of the user to thereby hold the wearable garment 100 in place on the appendage.

The wearable garment 100 also includes one or more relief zones 114 coupled to the sheath 102. The relief zones 114 include a second material. A pressure distribution of the second material of the relief zones 114 is greater than a pressure distribution of the first material of the sheath 102. As such, the second material of the relief zones 114 includes one or more pad structures, as shown labeled 114 in FIG. 4, shaped to be positioned adjacent one or more surfaces of a lower extremity. The sheath 102 and relief zones 114 are configured such that a peak localized pressure imparted by the first material in response to an externally applied force is greater than a peak localized pressure imparted by the second material in response to the externally applied force applied to the extremities of the wearer. Such an externally applied force may simply be from the pressure from the patient's foot resting on a mattress.

The second material may include a polyurethane foam, an encapsulated gel, an encapsulated liquid, a polymer, an encapsulated plasma, an encapsulated gas, or combinations thereof, among other possibilities. The second material may be encapsulated by an encapsulating material that is deformable, biocompatible and capable of compatibility with the gel, liquid, plasma, and/or gas. In such an example, a volume of the second material may be variable via injection or extraction of a gel, a liquid, a plasma or a gas into or out of the encapsulating material. Further, the encapsulating material may be self-sealing such that the encapsulating material may be externally accessed by an instrument (e.g., punctured by a needle) and then remain sealed upon removal of the instrument (e.g., needle). In addition, the wearable garment 100 may further include a one-way valve or a two-way valve coupled to the one or more relief zones 114 to permit an instrument to access the second material and thereby adjust a volume of the second material via injection or extraction. Other example arrangements are possible as well.

In various embodiments, the first and second materials, respectively, may comprise a breathable matrix and a polyurethane foam, a breathable matrix and an encapsulated gel, a breathable matrix and an encapsulated liquid, a breathable matrix and a polymer, a breathable matrix and an encapsulated plasma, a breathable matrix and an encapsulated gas, a cotton material and a polyurethane foam, a cotton material and an encapsulated gel, a cotton material and an encapsulated liquid, a cotton material and a polymer, a cotton material and an encapsulated plasma, a cotton material and an encapsulated gas, Polytetrafluoroethylene ("PTFE")vand a polyurethane foam, PTFE and an encapsulated gel, PTFE and an encapsulated liquid, PTFE and a polymer, PTFE and an encapsulated plasma, PTFE and an encapsulated gas, polyester and a polyurethane foam, polyester and an encapsulated gel, polyester and an encapsulated liquid, polyester and a polymer, polyester and an encapsulated plasma, polyester and an encapsulated gas, an elastic material and a polyurethane foam, an elastic material and an encapsulated gel, an elastic material and an encapsulated liquid, an elastic material and a polymer, an elastic material and an encapsulated plasma, or an elastic material and an encapsulated gas, among other possibilities.

As discussed above, the first material of the sheath 102 is different from the second material of the one or more relief zones 114 such that a pressure distribution of the second material is greater than a pressure distribution of the first material. The respective pressure distributions of the first and second materials may be controlled by the material properties, respective thicknesses of those materials or volume (in the case of an encapsulated second material) and/or thread count. The pressure distribution properties of a given material may be defined by a maximum localized pressure value experienced in response to a force applied to the given material. A peak localized pressure of the first material in response to an externally applied force is greater than a peak localized pressure of the second material in response to the externally applied force. Thus, the second material may distribute the applied force on the tissue of the user so as to reduce the peak localized pressure in response to the externally applied force to be less than a mean capillary perfusion pressure. In addition, the first material's peak localized pressure helps to maintain the wearable garment 100 in place on the respective body part on which the wearable garment 100 was disposed.

In one example, the wearable garment 100 further includes at least one second opening 116 in the second end 106 of the sheath 102. The at least one second opening 116 may include five openings each configured to receive a toe of a user. In another example, the at least one second opening 116 may be a single opening. In one example, the single opening may be configured to receive five toes of a user or to accommodate an appendage disposed through the cavity of the sheath, such as an arm or a leg. In yet another example, shown in FIGS. 1-6, and 11, the at least one second opening 116 is a single opening arranged adjacent to a medial side of the wearable garment 100 and configured to receive a hallux toe of a user. In yet another embodiment, the second end 106 of the sheath 102 is closed such that the sheath 102 is configured to cover the toes of a user, as shown in FIGS. 7-10.

The one or more relief zones 114 may take a variety of forms. In one example, the one or more relief zones 114 comprise at least one of a first distal metatarsal head zone 118, a fifth proximal and distal metatarsal head zone 120, a cuneiform zone 122, an anterior shin zone 124, an Achilles zone 126, a medial malleolus zone 128, a heel zone 130, a scaphoid tubercle zone 132, and a lateral malleolus zone 134. The first material may be positioned adjacent the surfaces of the lower extremity extending between and connecting the various relief zones 114, as shown in FIGS. 1-6. Though the edges of the second material may overlap with the first material for coupling. The second material is at a size and thickness necessary to adequately distribute the applied external force on the tissue of the user so as to reduce the localized pressure to be less than the mean capillary perfusion pressure, thereby reducing the risk of tissue necrosis. Further, the interior surface 136 of the sheath 102 may include an adhesive material to prevent the wearable garment 100 from slipping down the anterior shin of the user, for example. Such an adhesive material may include silicone, or any material with a moderate bio-adhesive nature, particularly a material that does not need to be wet to exhibit the bio-adhesive properties.

In another example, the first end 104 of the sheath 102 is configured to lie above a knee joint of a user, and the second end 106 of the sheath 102 is configured to lie below the knee joint of the user. In such an example, the one or more relief zones 114 comprise at least one of an anterior side, a posterior side, a medial side or a lateral side of a thigh region, a posterior side, a medial side or a lateral side of a calf region, a shin region, a knee cap region or a popliteal fossa region. In yet another example, the first end 104 of the sheath 102 is configured to lie above an elbow joint of a user, and the second end 106 of the sheath 102 is configured to lie below the elbow joint of the user. In such an example, the one or more relief zones 114 include at least one of a triceps zone, a biceps zone, a bursa zone, an ulna zone, a radius zone, and an olecranon zone.

In one example, the second material is coupled to an interior surface 136 of the first material. In another example, the second material may be layered between additional materials in the one or more relief zones 114. For example, the one or more relief zones 114 may be arranged such that the second material is disposed between two layers of the first material. In another example, the one or more relief zones 114 may include a layer of the first material having an inner surface coupled to a layer of the second material, where an inner surface of the second material is coupled to a layer of a bio-adhesive material arranged to interface with a user's appendage. In yet another example, the one or more relief zones 114 may include a layer of the first material having an inner surface coupled to a layer of the second material arranged to interface with the user's appendage. Other examples are possible as well.

In one example, the one or more relief zones 114 may be removably coupled to the interior surface 136 of the first material. In another example, the one or more relief zones 114 may be removably coupled to an exterior surface 138 of the first material. In such examples, the one or more relief zones 114 may include a plurality of hooks configured to removably couple with a plurality of loops on the first material. In another example, the one or more relief zones 114 may be removably coupled to the first material using one or more magnets, zippers, mechanical fasteners, buttons, an inferior glue, or any other nonpermanent reusable mechanical connection. Such embodiments may enable a medical professional to move the one or more relief zones 114 based on the particular patient. Further, such one or more relief zones 114 may be customizable such that the one or more relief zones 114 comprising the second material may be cut to allow for user specific customization. Such an embodiment may enable a medical professional to specifically tailor the size, shape, and/or thickness of the one or more relief zones 114 based on the particular patient.

In the example shown in FIGS. 1-6, the sheath 102 may include a foot region 140, a heel region 142, and a shin region 144. In such an example, the foot region 140 and the shin region 144 are coupled together via the heel region 142 such that the foot region 140 and the shin region 144 are arranged substantially perpendicular to one another. The outer perimeter of the plantar side 146 of the foot region 140 may have an oval shape, an elliptical shape or a plantar shape. The one or more relief zones 114 are coupled to at least one of a dorsal side 146, a medial side 148 or a lateral side 150 of the foot region 140, a posterior side 152, a medial side 154 or a lateral side 156 of the heel region 142, a posterior side 158, a medial side 160 or a lateral side 162 of the shin region 144 such that the one or more relief zones 114 are not arranged on a plantar side 164 of the foot region 140. In one particular example, as shown in FIGS. 7-10, the one or more relief zones 114 comprises a first relief zone 166 coupled to the medial side 148 of the foot region 140 of the sheath 102, a second relief zone 168 coupled to the lateral side 150 of the foot region 140 of the sheath 102, a third relief zone 170 coupled to the heel region 142 of the sheath 102, and a fourth relief zone 172 coupled to a shin region 144 of the sheath 102.

Further, the foot region 140 may be coupled to the heel region 142 via a first seam, and the shin region 144 may be coupled to the heel region 142 via a second seam. In such an example, the first seam and the second seam may be positioned on an outer surface 138 of the wearable garment 100 such that the seams do not contact the tissue of the user. Such a configuration may help prevent abrasion sores created by the seams being on the inside of the wearable garment 100.

The pressure distributing nature of the second material may reduce the user's ability to detect tactile sensations on the plantar surface of the foot. If this is the case, the user may have trouble walking and may be at risk for a fall. For this reason, in one example embodiment, the plantar surface 164 of the foot region 140 may include only the first material and/or a third material (described in more detail below), but not the second material.

Figure 1:
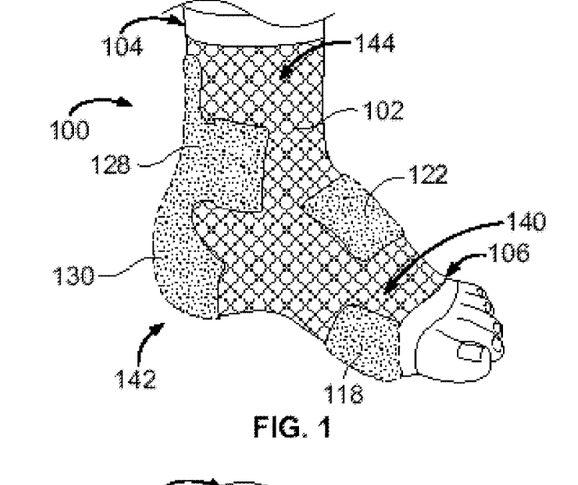
FIG. 1 is a medial perspective view of a wearable garment, according to an example embodiment.
Figure 2:
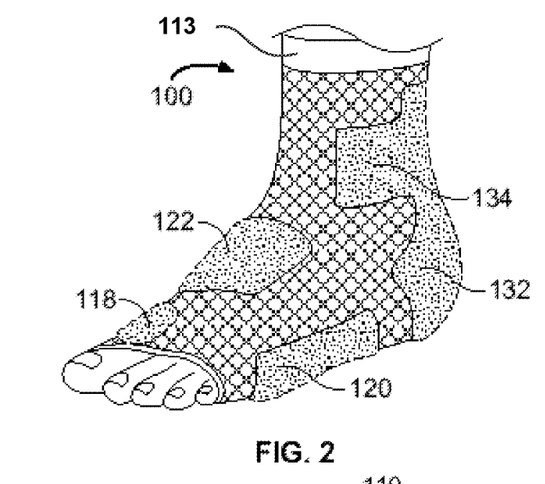
FIG. 2 is a lateral perspective view of the wearable garment, according to the example embodiment of FIG. 1.
Figure 3:
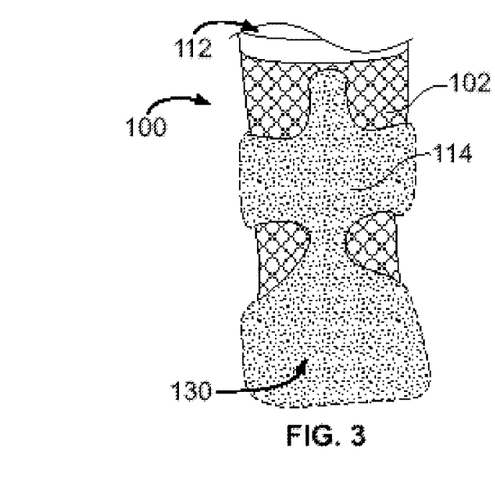
FIG. 3 a posterior view of the wearable garment, according to the example embodiment of FIG. 1.
Figure 4:
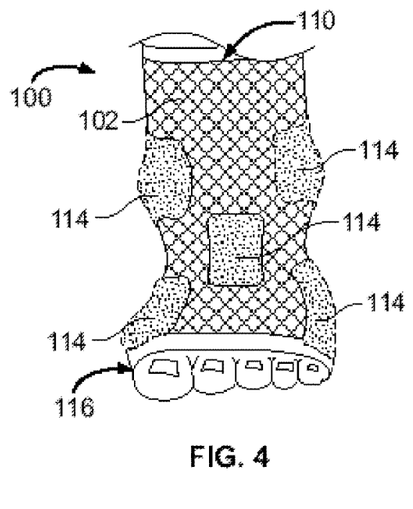
FIG. 4 is an anterior view of the wearable garment, according to the example embodiment of FIG. 1.
Figure 5:
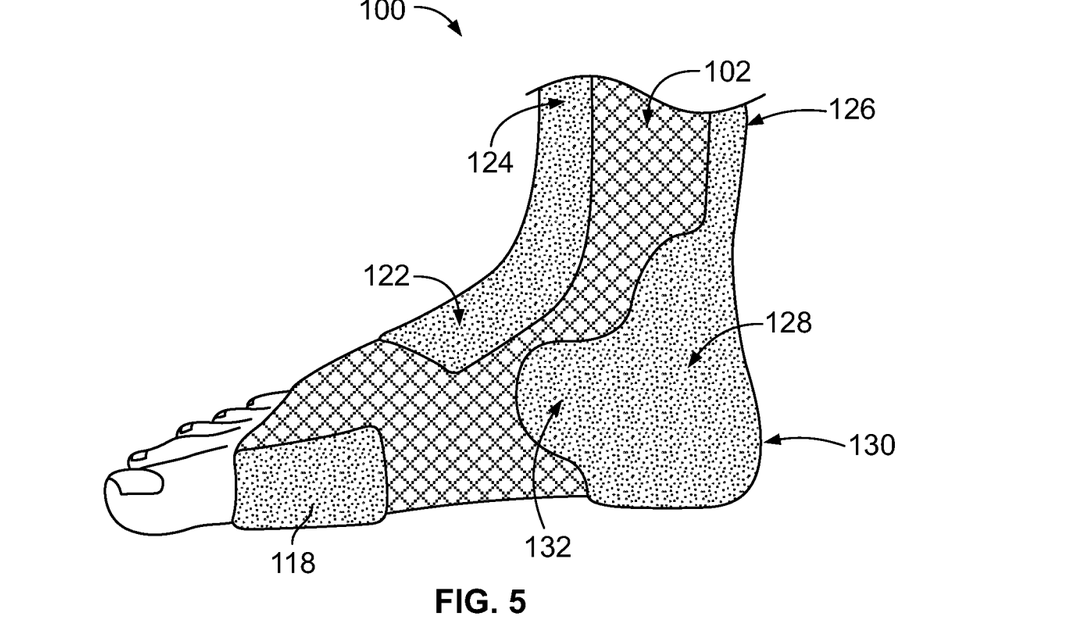
FIG. 5 is a medial side view of a wearable garment, according to an example embodiment.
Figure 6:
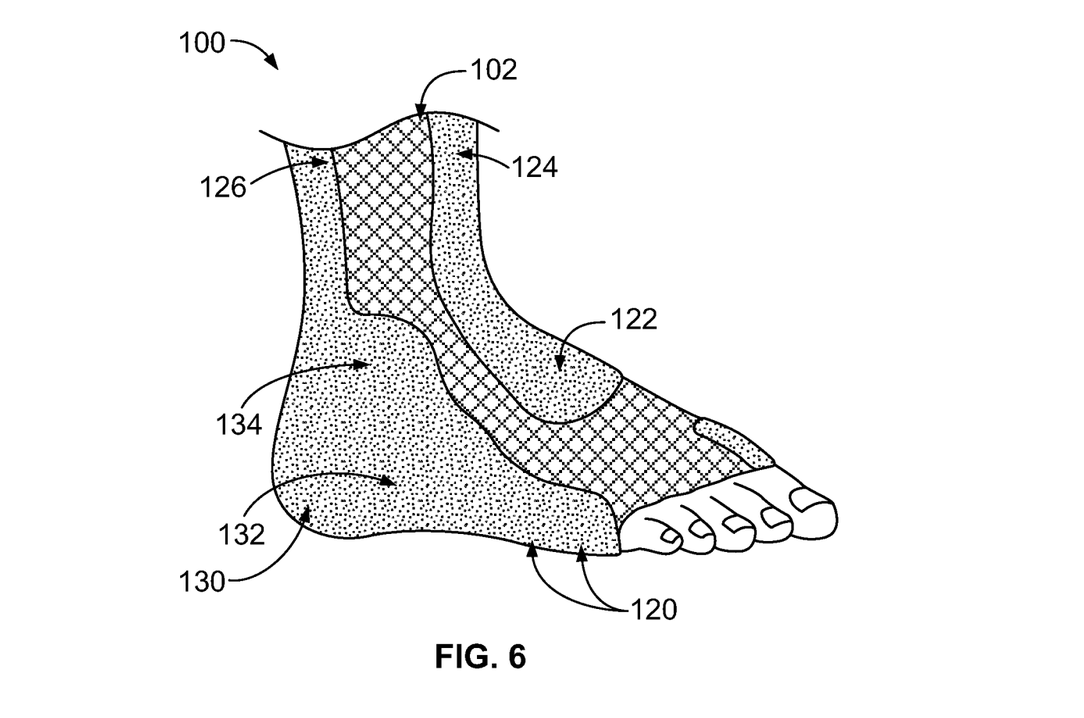
FIG. 6 is a lateral side view of the wearable garment, according to the example embodiment of FIG. 5.
Figure 7:
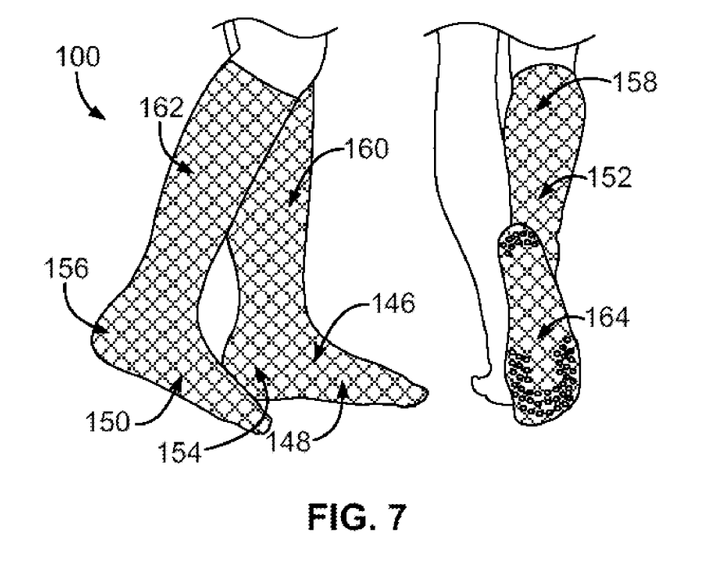
FIG. 7 is a lateral side view and bottom view of a wearable garment, according to an example embodiment.
Figure 8:
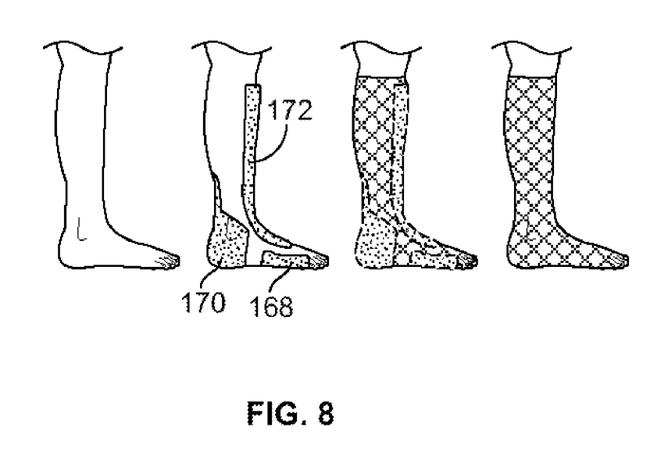
FIG. 8 is a lateral side view of the wearable garment, according to the example embodiment of FIG. 7.
Figure 9:
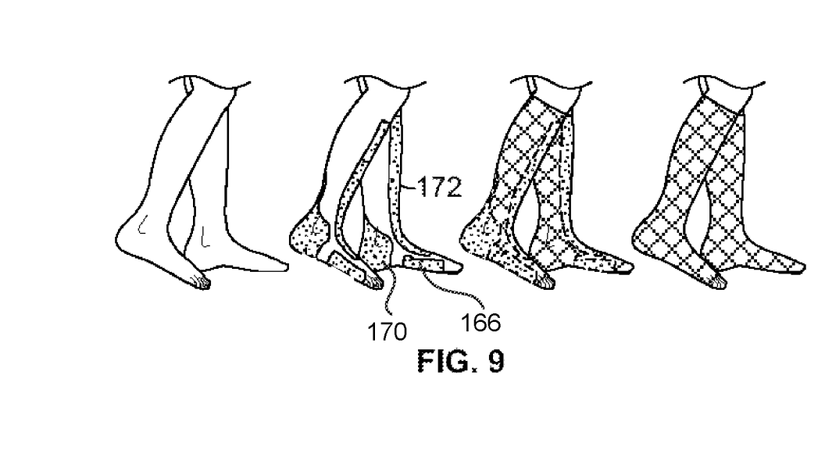
FIG. 9 is a lateral side view and medial side view of the wearable garment, according to the example embodiment of FIG. 7.
Figure 10:
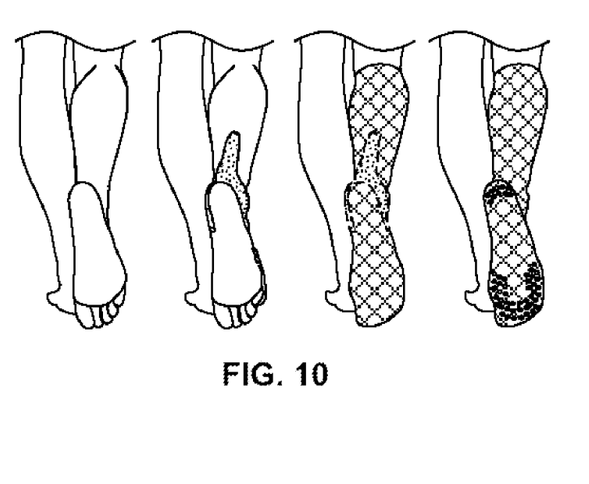
FIG. 10 is a bottom view of the wearable garment, according to the example embodiment of FIG. 7.

FIGS. 7-10 illustrate such an embodiment. As shown in FIGS. 7-10, the one or more relief zones 114 of the wearable garment 100 are coupled to at least one of a dorsal side 146, a medial side 148 or a lateral side 150 of the foot region 140, a posterior side 152, a medial side 154 or a lateral side 156 of the heel region 142, a posterior side 158, a medial side 160 or a lateral side 162 of the shin region 144 such that the one or more relief zones 114 are not arranged on a plantar side 164 of the foot region 140. As such, as shown in FIGS. 7-10, the one or more relief zones 114 may be absent from a bottom surface or plantar surface 164 of the sheath 102. Such an embodiment may beneficially increase the ability of a user to sense a surface upon which he/she walks. In such an example, the bottom surface or plantar surface 164 of the sheath 102 may include a third material to provide a gripping interface to frictionally engage the surface on which the user is walking. As such, the third material may be on an outer surface of the sheath 102. In such an example, the third material has a higher coefficient of friction than the first material. In one example, the third material may comprise a non-skid material such as silicone, neoprene, fluoroelastomer, fluorosilicone, or plastisol inks, although other non-skid materials are possible as well. The third material may be patterned or coat the entire surface of the plantar surface 164 of the sheath 102. In one particular example, as shown in FIGS. 7 and 10, the bottom surface of the sheath may include a plurality of silicone protrusions to provide the gripping interface. Other arrangements of the third material are possible as well. Further, as shown in FIGS. 7-10, the second end 106 of the sheath 102 of the wearable garment 100 may be closed, thereby concealing a user's toes. In such an example, the sheath 102 is configured to cover the toes of a user like a sock.

Figure 11:
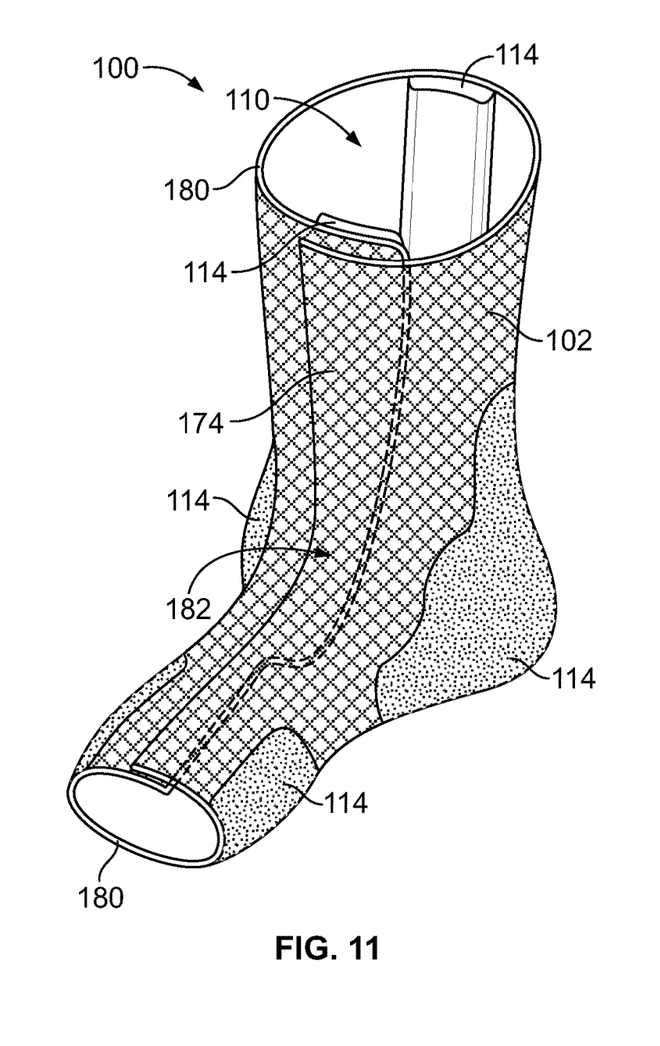
FIG. 11 is a medial perspective view of a wearable garment, according to an example embodiment.
Figure 12:
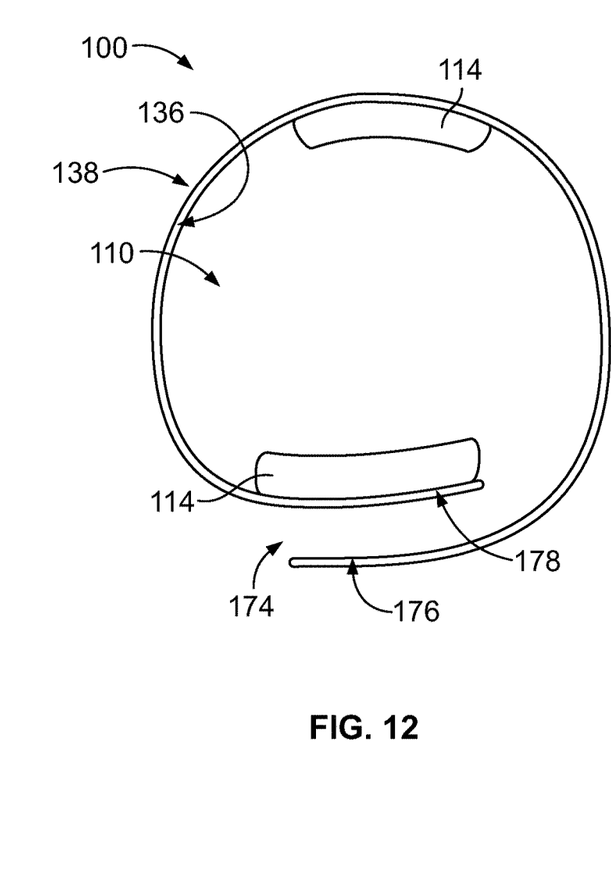
FIG. 12 is a top view of the wearable garment, according to the example embodiment of FIG. 11.

FIGS. 11-12 illustrate yet another embodiment of the wearable garment 100. As shown in FIGS. 11-12, the wearable garment may include a separable seam 174 extending from the first end 104 to the second end 106. In the example shown in FIG. 11, the separable seam 174 is on the anterior side of the wearable garment 100. The separable seam 174 may enable the wearable garment 100 to transition from a closed state where the wearable garment 100 forms a tubular structure to an open state where the wearable garment 100 forms a semi-tubular or semi-flat structure with optional preformed contours to receive such areas like the heel, medial/lateral malleolus, and medial/lateral metatarsal heads. As such, a medical professional may separate the separable seam 174 to transition the wearable garment 100 to the open state to place the wearable garment 100 on a patient, and then close the separable seam 174 once the wearable garment 100 is positioned on the patient to transition the wearable garment 100 to the closed state, thereby securing the wearable garment 100 to the patient. In such an example, as shown in FIG. 12, the one or more relief zones 114 may include at least a relief zone on an anterior side of the wearable garment 100, positioned posterior to the separable seam 174. In such an example, the relief zone 114 is positioned under the separable seam 174, closest to the skin of the patient. This arrangement ensures that the separable seam 174 does not contact the tissue of the user. Such a configuration may help prevent abrasion sores that would otherwise be created by the separable seam 174 being arranged on the inside of the wearable garment 100.

As shown in FIG. 12, a first portion 176 of the wearable garment 100 overlaps with a second portion 178 of the wearable garment 100 to form the separable seam 174. As shown in FIG. 12, the first portion 176 may be on an anterior side of the wearable garment 100, while the second portion 178 is posterior to the first portion 176. The first portion 176 may be separably coupled to the second portion 178 in a variety of ways, including one of a hook and fastener system, a mechanical fastener, a zipper, a string, one or more straps, one or more magnets, an inferior glue, or any other nonpermanent reusable mechanical connection. Further, the wearable garment 100 may include one or more shape-memory rings 180 positioned at one or more of the first end 104, the second end 106, or a middle section 182 of the wearable garment 100. The shape-memory ring 180 may include nitinol, as an example, although other materials are possible as well. Such a shape-memory ring 180 may cause the wearable garment 100 to bias to the closed position.

One example method for limiting development of tissue necrosis in a subject in need thereof includes determining, from a plurality of sized wearable garments of any one of the foregoing embodiments, an appropriately sized wearable garment to fit a foot of the subject, positioning the wearable garment on the foot of the subject, and maintaining the wearable garment on the foot of the subject for a period of time and under conditions effective to limit development of tissue necrosis. In one example, there may be a plurality of sized wearable garments, such as a small, medium, large, and extra-large size depending on the patient. In another example, the sheath 102 may be customizable such that the sheath 102 may be cut to allow for user specific customization.

In another embodiment, the method may further comprise securing the wearable garment to the subject via one or more of an elastic band and stretchable stitching surrounding the at least one opening at the second end of the wearable garment. In such an example, the wearable garment may include one or more of an elastic band 113, straps, and stretchable stitching at the first end of the sheath surrounding the first opening that is configured to receive a user's foot and ankle therethrough. As another example, the wearable garment may include one or more of an elastic band, straps, and stretchable stitching surrounding the at least one second opening at the second end of the wearable garment to receive one or more toes of a user. Such configurations would enable the user to adjust the fit of the wearable garment to ensure the wearable garment stays secure to the lower extremity.

It will be appreciated that other arrangements are possible as well, including some arrangements that involve more or fewer steps than those described above, or steps in a different order than those described above.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the claims.

The invention claimed is:

1. A wearable garment comprising:
a sheath having a first end and a second end, wherein the sheath defines a cavity in a wearable position configured to receive an appendage of a user, wherein the sheath has a first opening at the first end, wherein the sheath comprises a first layer and a second layer, the first layer comprising a first material, and wherein the second layer of the sheath is configured to contact the appendage of the user when in use; and
one or more relief zones coupled to the sheath, wherein the one or more relief zones comprise a second material different from the first material, wherein the second material comprises a gel, wherein the second material of the one or more relief zones is arranged between the first layer and the second layer of the sheath, wherein a pressure distribution of the second material is greater than a pressure distribution of the first material, wherein the one or more relief zones comprise a first relief zone configured to cover a first metatarsal head of the user, a second relief zone configured to cover a fifth metatarsal head of the user, a third relief zone configured to cover a medial malleolus, a lateral malleolus, and a heel of the user, and a fourth relief zone configured to cover a cuneiform and a shin of the user, wherein the first material surrounds each of the first relief zone, the second relief zone, the third relief zone, and the fourth relief zone such that each relief zone is separated from each of the other relief zones by the first material, wherein an interior surface of the second layer of the sheath includes an adhesive material configured to contact the shin of the user to prevent the wearable garment from slipping down the shin of the user, wherein the gel is encapsulated by an encapsulating material that is deformable and biocompatible, and wherein the encapsulating material is self-sealing such that the encapsulating material may be externally accessed by a needle and then remain sealed upon removal of the needle such that a volume of the gel is variable.

2. The wearable garment of claim 1, wherein the first material has an elastic property such that the sheath is configured to expand to receive the appendage of the user, and thereafter retract to conform to the appendage to thereby hold the wearable garment in place on the appendage.

3. The wearable garment claim 1, further comprising:
a separable seam extending from the first end to the second end.

4. The wearable garment of claim 3, wherein the one or more relief zones comprise at least an anterior side of the wearable garment, positioned posterior to the separable seam.

5. The wearable garment of claim 3, wherein the separable seam comprises one of a hook and fastener system, a mechanical fastener, a zipper, a string, one or more straps, one or more magnets, or an interior glue.

6. The wearable garment of claim 1, wherein the second material is configured to reduce a peak localized pressure from a weight of the appendage resting on a surface to be less than a mean capillary perfusion pressure.

7. The wearable garment of claim 1, wherein the second end of the sheath has at least one second opening.

8. The wearable garment of claim 7, wherein the at least one second opening comprises five openings each configured to receive a toe of the user.

9. The wearable garment of claim 7, wherein the at least one second opening is a single opening.

10. The wearable garment of claim 9, wherein the single opening is arranged adjacent to a medial side of the sheath and configured to receive a hallux toe of the user.

11. The wearable garment of claim 1, further comprising one or more of an elastic band and stretchable stitching surrounding the first opening.

12. The wearable garment of claim 1, further comprising one or more of an elastic band and stretchable stitching surrounding the at least one second opening at the second end of the sheath.

13. The wearable garment of claim 1, wherein the second end of the sheath is closed such that the sheath is configured to cover the toes of the user.

14. The wearable garment of claim 1, wherein the wearable position further comprises a calf region and a foot region, wherein the calf region and the foot region are being perpendicular to one another.

15. The wearable garment of claim 1, wherein the first material comprises a breathable matrix, a cotton material, Polytetrafluoroethylene (PTFE), polyester, an elastic material, or combinations thereof.

16. The wearable garment of claim 1, wherein a bottom surface of the foot region of the sheath comprises a third material having a higher coefficient of friction than the first material.

17. The wearable garment of claim 16, wherein the third material comprises silicone, neoprene, fluoroelastomer, fluorosilicone or plastisol inks.

\* \* \* \* \*